United States Patent [19]

Morscher

[11] Patent Number: 4,718,916
[45] Date of Patent: Jan. 12, 1988

[54] FEMUR HEAD PROSTHESIS

[75] Inventor: Erwin W. Morscher, Basel, Switzerland

[73] Assignees: Sulzer Brothers Ltd., Winterthur; Protek AG, Berne, both of Switzerland

[21] Appl. No.: 870,091

[22] Filed: Jun. 3, 1986

[30] Foreign Application Priority Data

Jun. 12, 1985 [CH] Switzerland .................. 2476/85

[51] Int. Cl.$^4$ ............................................. A61F 2/32
[52] U.S. Cl. ............................................. 623/23
[58] Field of Search ........................... 623/23, 22

[56] References Cited

U.S. PATENT DOCUMENTS

| 3,987,499 | 10/1976 | Scharbach | 623/23 |
| 4,619,659 | 10/1986 | Witzel | 623/23 |
| 4,642,124 | 2/1987 | Cooke | 623/23 |
| 4,657,552 | 4/1987 | Karpf | 623/23 |

Primary Examiner—Gregory E. McNeill
Attorney, Agent, or Firm—Kenyon & Kenyon

[57] ABSTRACT

The total implant is constructed of a prosthesis shank, a U-shaped plastic insert which envelops the proximal region of the shank, a deformable sheet metal jacket about the plastic insert and a pair of wedges which are driven into a space between the sides of the prosthesis shank and the sheet metal jacket in order to expand the jacket against the bone during implantation. A guide sleeve is also disposed at the distal end of the shank to slidably receive and guide the distal end of the shank.

13 Claims, 11 Drawing Figures

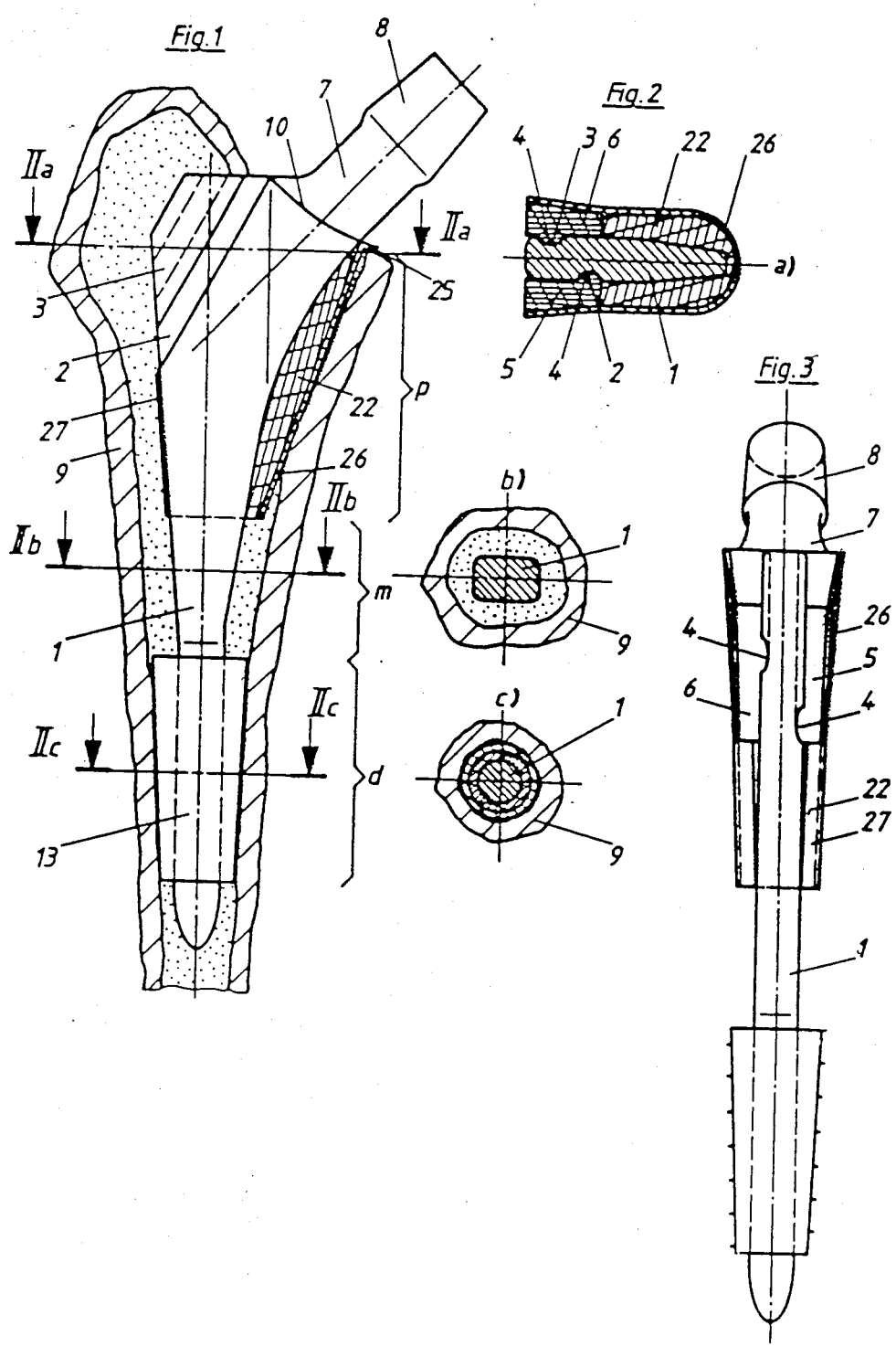

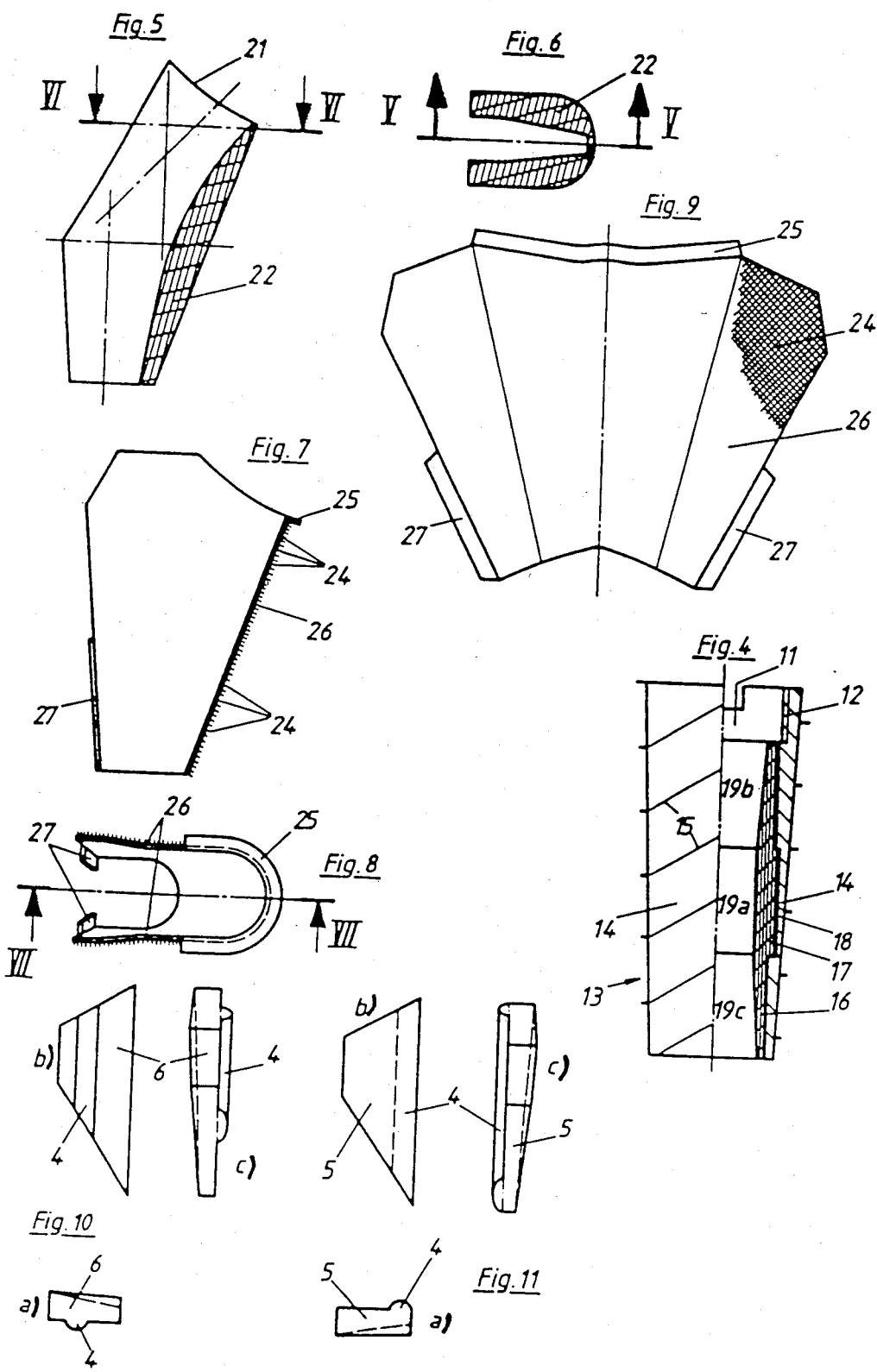

FEMUR HEAD PROSTHESIS

This invention relates to a femur head prosthesis.

As is known, various types of femur head prostheses have been known for implanting in a femur. Further, various types of techniques have been known for aring these prostheses in a bone. For example, European Patent Application No. 041,820 describes a femur head prosthesis having a straight blade type shank which is guided in a distal region by a sleeve in a radially centered and axially movable manner. In addition, the prosthesis is laterally wedged in a proximal region by means of anchoring wedges which are driven into the sides of the blade and which are situated laterally of a prosthesis neck axis and inclined relative to the shank axis under a similar angle as the neck axis.

Based on recent studies—Chr.v. Hasselbach, U. Witzel, "Comparative stress analyses on various hip endoprostheses" published in the journal "Unfallheilkunde" (Accident Therapeutics) 97, 1984, pages 205–215—it has been suggested to anchor a femur head prosthesis in the proximal region of its shank in such a way that a distribution of the forces "flowing" from the implant to the bone can be approximated to the natural stress so that bone atrophy, especially in the calcar arc, is to be prevented. In addition, relative movements in the interface between implant and bone are avoided while the shank itself is supported in a slide bearing. Further, it is suggested that the high modulus of elasticity of the shank, generally made of metal, is approximated "on the way" to the interface of that of the bone substance.

Accordingly, it is an object of the invention to provide a femur head prosthesis which can be anchored in a cement-free manner to avoid bone atrophy.

It is another object of the invention to provide a technique for anchoring a femur head prosthesis in a manner so that the elasticity of the total implant approximates the elastic properties of the femur.

It is another object of the invention to be able to distribute a flow of forces between an implant and a bone in a manner to simulate a natural flow of stress.

Briefly, the invention provides a total implant which is comprised of a femur head prosthesis having a shank, a neck and a collar-like projection between the shank and neck, a plasti insert for elastically supporting a proximal region of the shank in a medial direction, a deformable sheet metal jacket for enveloping the insert and the prosthesis and which is open on a lateral narrow side and a pair of wedges for positioning between the shank and the jacket in order to laterally widen the jacket after positioning of the prosthesis, insert and jacket in place.

The collar-like projection of the prosthesis is formed with a convex cylindrical partial surface on a side facing the femur bone while the plastic insert has a concave counter-surface to receive the convex surface of the prosthesis. In addition, the jacket is provided with a proximal edge which is bent at an angle near the plastic insert for seating on a cortical in a re-section plane of the femur.

The sheet metal jacket is made of thin wall construction and consists perferrably of titanium or a titanium alloy. When the total implant is being implanted, the wedges expand the sheet metal jacket and thereby firmly anchor the jacket in the bone. Hence, as required, relative movements in the interface between the bone and implant are avoided. However, relative movements are permitted between the sheet metal jacket and the plastic insert and mainly between the shank and the plastic insert.

The total implant also includes a sleeve for slidably receiving and guiding a distal end of the shank, for example, as described in European Patent Application No. 0086879. In this case, the plastic insert and the distal sleeve form an elastic bearing for the shank to permit axial sliding movements.

The plastic insert is made predominantly of polyethylene and has a modulus of elasticity which is considerably lower than that of the shank material. This brings about an approximation of the modulus of elasticity of the total implant to that of the bone. Furthermore, the cylindrical partial surface of the collar-like projection and the counter surface of the plastic insert permit bending moments to cause a "rolling off" of the shank on the insert without shearing forces being exerted on the bone. The transverse forces resulting from the "rolling off" due to the occurring bending moment are absorbed via the distal sleeve by the cortical tissue of the femur bone.

The required immobile anchoring of the sheet metal jacket at the bone tissue can be improved by providing the outerside of the sheet metal jacket, at least partially, with a structure that promotes the accretion and growing in of tissue. Such a structure may consist, for example, of a wire mesh or grid.

These and other objects and advantages of the invention will become more apparent from the following detailed description taken in conjunction with the accompanying drawings wherein:

FIG. 1 illustrates a longitudinally sectioned femur bone having a total implant therein in accordance with the invention;

FIG. 2a illustrates a view taken on line IIa—IIa of FIG. 1;

FIG. 2b illustrates a view taken on line IIb—IIb of FIG.1;

FIG. 2c illustrates a view taken on line IIc—IIc of FIG. 1;

FIG. 3 illustrates a view of the total implant taken from the left of FIG. 1;

FIG. 4 illustrates a partial sectional view of a distal sleeve in accordance with the invention;

FIG. 5 illustrates a view taken on line V—V of FIG. 6 of the medial plastic insert;

FIG. 6 illustrates a view taken on line VI—VI of FIG. 5;

FIG. 7 illustrates a view taken on line VII—VII of FIG. 8 of the sheet metal jacket of FIG. 1;

FIG. 8 illustrates a top view of the jacket of FIG. 7;

FIG. 9 illustrates a developed view of the sheet metal jacket in accordance with the invention;

FIG. 10a illustrates a top view of a wedge in accordance with the invention;

FIG. 10b illustrates a front view of the wedge of FIG. 10a;

FIG. 10c illustrates a side view of the wedge of FIG. 10a;

FIG. 11a illustrates a top view of a second wedge employed in the implant;

FIG. 11b illustrates a front view of the wedge of FIG. 11a; and

FIG. 11c illustrates a side view of the wedge of FIG. 11a.

Referring to FIG. 1, the total implant includes a femur head prosthesis having a shank 1, a neck 7 and a collar-like projection 10 between the shank 1 and neck 7 which serves as a transition between the shank 1 and the neck 7. The shank 1 is preferrably made of titanium or a titanium alloy and is implanted in a femur bone 9.

As indicated in FIGS. 1 and 2c, the distal region d of the shank 1 has a constant circular cross section while, as indicated in FIG. 2b, a central transitional region m has a rectangular shaped cross section which changes over into a blade-like straight shank in the proximal region p as indicated in FIG. 2a.

The sides of the shank which are directed toward anterior and toward posterior, respectively, each contain a lateral groove 2, 3. The shank 1 ends proximally in a horizontal shoulder which changes over into the neck 7 which, in turn, merges into a conical pin or peg 8 for receiving a joint head (not shown). The collar-type projection 10 in anterior/posterior view is rounded in a circular-cylindrical form.

As indicated in FIGS. 1, 2 and 3, a pair of wedges 5, 6 each of which includes a guiding bead 4 is positioned at the sides of the shank 1 with the respective bead 4 received in the grooves 2, 3 of the blade sides. In addition, a medial plastic insert 22 of substantially U-shape is disposed in the proximal region p of the shank. As indicated in FIG. 5, the plastic insert 22 has a shell surface 21 which corresponds to the circular-cylindrical form of the projection 10 when the prosthesis is implanted. As indicated in FIG. 1, the collar-like projection 10 has a convex cylindrical partial surface on the side facing the bone 9 which is received in a concave counter-surface 21 of the plastic inset 22 (FIG. 5).

Referring to FIGS. 5 and 6, the plastic insert 22 is of generally U-shape with a web section which connects the legs of the shape. In addition, as indicated in FIG. 5, the web thickens from the upper end towards the middle and thereafter tapers to a thinner thickness at the lower end. In addition, the overall shape of the insert, as viewed in FIG. 5, tends to follow the axes of the prosthesis neck and the prosthesis shank.

Referring to FIGS. 2 and 3, the total implant also includes a deformable sheet metal jacket 26 which is disposed to envelope the plastic insert 22 and the prosthesis. This jacket 26 is made of a thin deformable sheet of pure titanium or a titanium alloy. As shown in FIGS. 7 to 9, the form of the jacket 26 which is shown therein terminates medially with a proximal edge 25 which is to lie on the hard cortical of the bone 9. In the distal-lateral direction, the sides of the jacket 26 are bent as hooks at the end 27. Thus, as can be seen from FIGS. 5 to 7, the hook ends 27 are to embrace the plastic insert 22. In order to promote the accretion and growing in of bone tissue, the jacket 26 is provided on the outside with a structure which is made from a wire grid or wire mesh 24 of pure titanium.

As indicated in FIG. 8, the side walls of the jacket 26 are tapered inwardly in a downward direction to envelop the plastic insert 22 and to cooperate with the wedges 5, 6 (see FIG. 3). This jacket is also open on the lateral narrow side.

Referring to FIGS. 10 and 11, the wedges 5, 6, are shaped in similar fashion so as to be fitted between the sides of the sheet metal sleeve 26 and the sides of the prosthesis shank. In addition, each has an elongated bead for extending along one side surface. These wedges 5, 6 are driven into the space between the jacket 26 and the shank 1 when the total implant is being implanted. Because the wedges widen from the distal end to the proximal end, as shown in FIGS. 10c and 11c, respectively, the wedges 5, 6 expand the jacket 26 while being guided within the grooves 2, 3 of the shank in order to press the jacket against the osseous wall of the bone cavity. In this matter, intimate contact between the jacket 26 and the bone 9 results. This, in turn, promotes the accretion and growing in of tissue. In addition, the required elastic support of the shank is ensured proximally by the elasticity of the insert 22 on which the shank 1 rests directly and exclusively.

Referring to FIG. 1, the total implant also includes a guide sleeve 13 which slidably receives and guides the distal end of the shank 1 in the distal region d. As further indicated in FIG. 4, the sleeve is comprised of a metallic outer jacket 14, for example of titanium, on which a sharp-edged self-cutting thread 15 is provided on the outer surface in order to enable the jacket 14 to be screwed into the cortical bone by means of an inserting or screwing-in instrument having a threaded head. As indicated, a groove 11 is provided in the jacket 14 to engage the instrument while also being provided with a thread 12 at the upper end to threadably receive the instrument before the jacket 14 is inserted into the surgically opened opening in the bone 9 and before the thread 15 cuts into the bone.

The sleeve 13 also has an inner sleeve 16 within the jacket 14 which is made of polyethylene and which is pressed into the jacket 14 prior to anchoring of the jacket 14 in the bone 9. As indicated, the inner sleeve 16 has a projection 17 which snaps elastically into a depression in the outer jacket 14. This inner sleeve 16 prevents a direct rubbing of the two metal surfaces of the outer jacket 14 and the shank 1. Further, the cavity of the inner sleeve 16 is divided into three regions. A central cylindrical region 19a is so adapted to the diameter of the distal shank region that the shank can be slidably moved by hand in the inner sleeve 16 without "wobbling" therein. The outer cavity regions 19b, 19c are slightly conical to avoid jamming of the shank 1, for example in the case of imprecise fit of the sleeve 13.

In inplanting the total implant, the guide sleeve 13 is initially put in place in a known manner. Thereafter, the plastic insert 22 and sheet metal jacket 26 are placed about the shank 1 of the prosthesis and the resulting unit is then put in to place in the bone 9 so that the distal end of the shank 1 is slid into the guide sleeve 13. At this time, the proximal edge 25 of the jacket 26 is brought to lie on the hard cortical of the bone 9 as indicated in FIG. 1. Thereafter, the wedges 5, 6 are inserted into the space between the sheet metal jacket 26 and the sides of the blade shank by being slid via the beads 4 into the respective grooves 2, 3.

The prosthesis shank is thus supported in an axially movable manner in the proximal region p on the elastic plastic insert 22 so that the flow of force is transmitted essentially over the circular-cylindrical surfaces 10, 21 of the prostheses and the plastic insert. Further, the flow of force on the loaded surface of the plastic insert is distributed relatively evenly onto the bone 9 so that bone atrophy, particularly in the region of the calcar arc is avoided. Still further, the elasticity of the total implant is approximated to the elastic properties of the bone.

What is claimed is:
1. In combination
   a femur head prosthesis having a straight blade-type shank, a neck and a collar-like projection between said shank and said neck with a convex cylindrical partial surface on a side facing a femur bone;

a plastic insert for elastically supporting a proximal region of said shank in a medial direction, said insert having a concave counter-surface to receive said convex surface of said projection;

a deformable sheet metal jacket for enveloping said insert and said prosthesis and being open on a lateral narrow side, said jacket having a proximal edge being bent at an angle near said insert for seating on a cortical; and a pair of wedges for positioning between said shank and said jacket to laterally widen said jacket after positioning of said prosthesis, insert and jacket in place.

2. The combination as set forth in claim 1 wherein said jacket has an outer surface of a structure to promote accretion and growing in of tissue.

3. The combination as set forth in claim 2 wherein said structure is one of a wire mesh and a wire grid.

4. The combination as set forth in claim 1 which further comprises a sleeve for slidably receiving and guiding a distal end of said shank.

5. In combination
a femur head prosthesis having a shank, a neck and a collar-like projection between said shank and said neck;

a plastic insert for elastically supporting a proximal region of said shank in a medial direction in a femur bone;

a deformable sheet metal jacket for enveloping said insert and said prosthesis and being open on a lateral narrow side; and a pair of wedges for positioning between said shank and said jacket to laterally widen said jacket after positioning of said prosthesis, insert and jacket in place.

6. The combination as set forth in claim 5 wherein said shank has a groove in each of two lateral sides and each wedge has a bead slidably received in a respective groove to guide said wedge during a wedging-in movement between said jacket and said shank.

7. The combination as set forth in claim 6 wherein each groove is angularly disposed to a longitudinal axis of said shank.

8. The combination as set forth in claim 5 which further comprises a sleeve for slidably receiving and guiding a distal end of said shank.

9. The combination as set forth in claim 5 wherein said jacket has an outer surface of a structure to promote accretion and growing-in of tissue.

10. The combination as set forth in claim 9 wherein said structure is one of a wire mesh and a wire grid.

11. The combination as set forth in claim 5 wherein said jacket is made of a metal selected from the group consisting of titanium and titanium alloys.

12. The combination as set forth in claim 5 wherein said shank has a distal region of constant circular cross-section, a central transitional region of rectangular cross-section and a straight proximal region.

13. The combination as set forth in claim 12 which further comprises a sleeve for slidably receiving said distal region of said shank, said sleeve including a metal outer jacket having a self-cutting thread and a plastic liner in said outer jacket for slidaby receiving said shank.

* * * * *

UNITED STATES PATENT AND TRADEMARK OFFICE
CERTIFICATE OF CORRECTION

PATENT NO. : 4,718,916

DATED : January 12, 1988

INVENTOR(S) : ERWIN W. MORSCHER

It is certified that error appears in the above-identified patent and that said Letters Patent is hereby corrected as shown below:

Column 1, line 7 "aring" should be -anchoring-
Column 1, line 46 "plasti" should be -plastic- Signed and Sealed this Fourth Day of October, 1988

Attest:

DONALD J. QUIGG

*Attesting Officer*      *Commissioner of Patents and Trademarks*